(12) United States Patent
Catron

(10) Patent No.: US 7,654,388 B2
(45) Date of Patent: Feb. 2, 2010

(54) APPARATUS TO SECURE AND FACILITATE THE INVENTORY OF MEDICATIONS IN EMERGENCY MEDICAL SERVICES VEHICLES

(76) Inventor: Ernest D. Catron, 8727 Bass Lake Dr., New Port Richey, FL (US) 34654

(*) Notice: Subject to any disclaimer, the term of this patent is extended or adjusted under 35 U.S.C. 154(b) by 511 days.

(21) Appl. No.: 11/544,217

(22) Filed: Oct. 6, 2006

(65) Prior Publication Data

US 2008/0093365 A1 Apr. 24, 2008

(51) Int. Cl.
A45C 13/10 (2006.01)
A45C 13/18 (2006.01)

(52) U.S. Cl. ............... 206/1.5; 206/538; 70/158; 220/345.2

(58) Field of Classification Search ............... 206/1.5, 206/528, 538, 539, 561; 70/63, 158, 163, 70/164, 166, 167, 168; 109/45, 52; 220/345.1, 220/345.2, 345.3, 345.4, 254.1, 254.9, 255
See application file for complete search history.

(56) References Cited

U.S. PATENT DOCUMENTS 2,035,340 A * 3/1936 Primavera ............... 206/431
3,441,165 A * 4/1969 Zampichelli ............ 220/787
4,062,445 A * 12/1977 Moe ........................ 206/1.5
4,101,052 A * 7/1978 Dove ....................... 229/101
4,524,904 A 6/1985 Masse et al.
4,872,559 A * 10/1989 Schoon .................... 206/538
D308,276 S 5/1990 Appelbaum
4,926,762 A 5/1990 Paul
4,986,589 A 1/1991 McNew
D325,125 S 4/1992 Paul
5,154,497 A 10/1992 Smith
5,242,076 A * 9/1993 Gibilisco ................. 220/525
5,263,578 A * 11/1993 Narvey .................... 206/232
D342,892 S * 1/1994 Teerds ..................... D9/759
D368,249 S 3/1996 Ferrer
5,577,629 A * 11/1996 Rosler ..................... 220/525
6,000,546 A * 12/1999 Noble ...................... 206/538
6,082,601 A * 7/2000 Standish .................. 224/569
6,164,219 A 12/2000 Green

* cited by examiner

*Primary Examiner*—Mickey Yu
*Assistant Examiner*—Chun Cheung
(74) *Attorney, Agent, or Firm*—Pennington, Moore, Wilkinson, Bell & Dunbar, P.A.; Sidney W. Kilgore

(57) ABSTRACT

A clear, lockable, sealable container for the storage of controlled substances in ambulances and other emergency medical vehicles, allowing paramedics and other emergency medical personnel to inspect and inventory readily the pharmaceuticals in the container without opening, unlocking, or breaking the seal on the container.

13 Claims, 6 Drawing Sheets

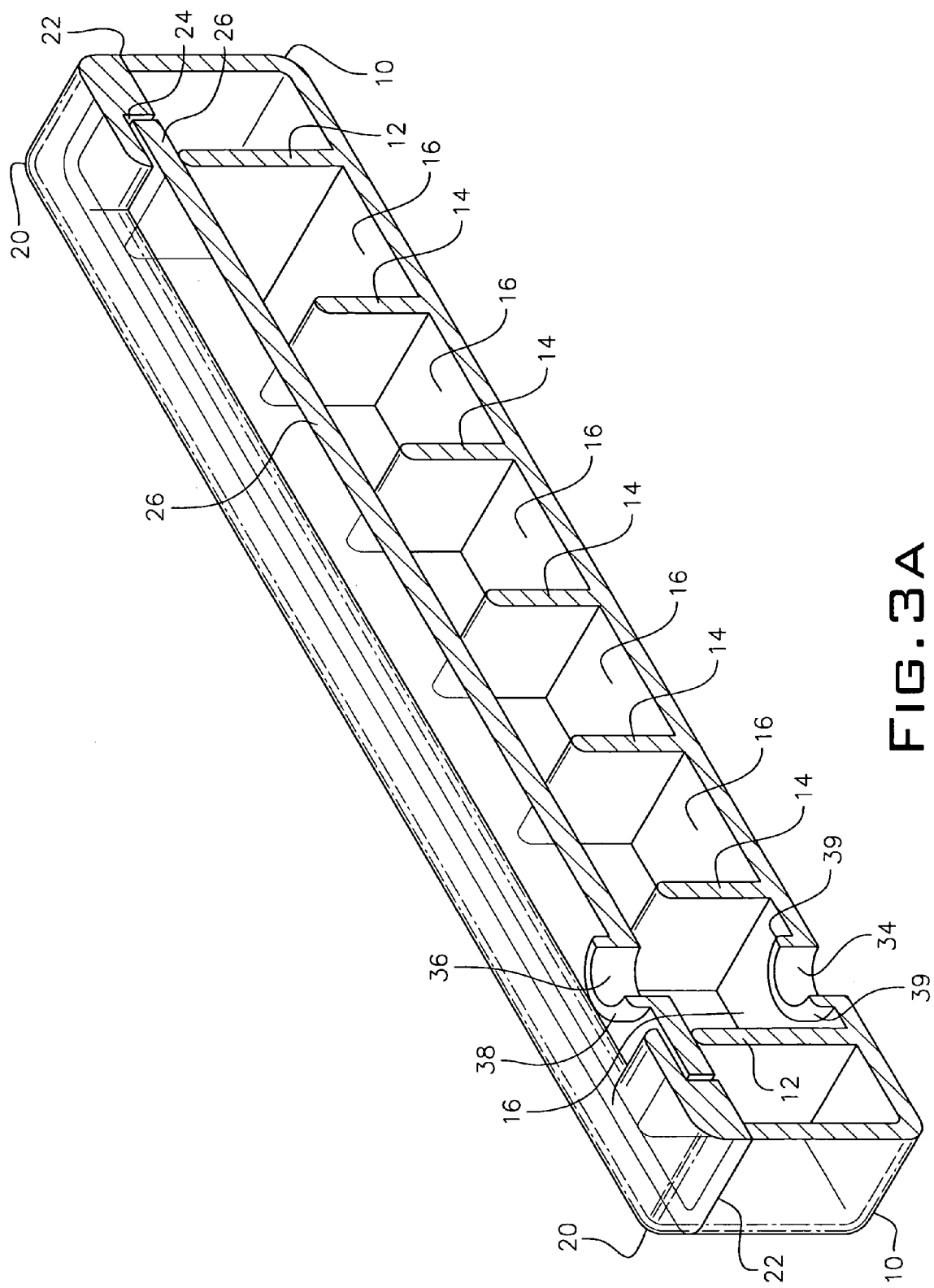

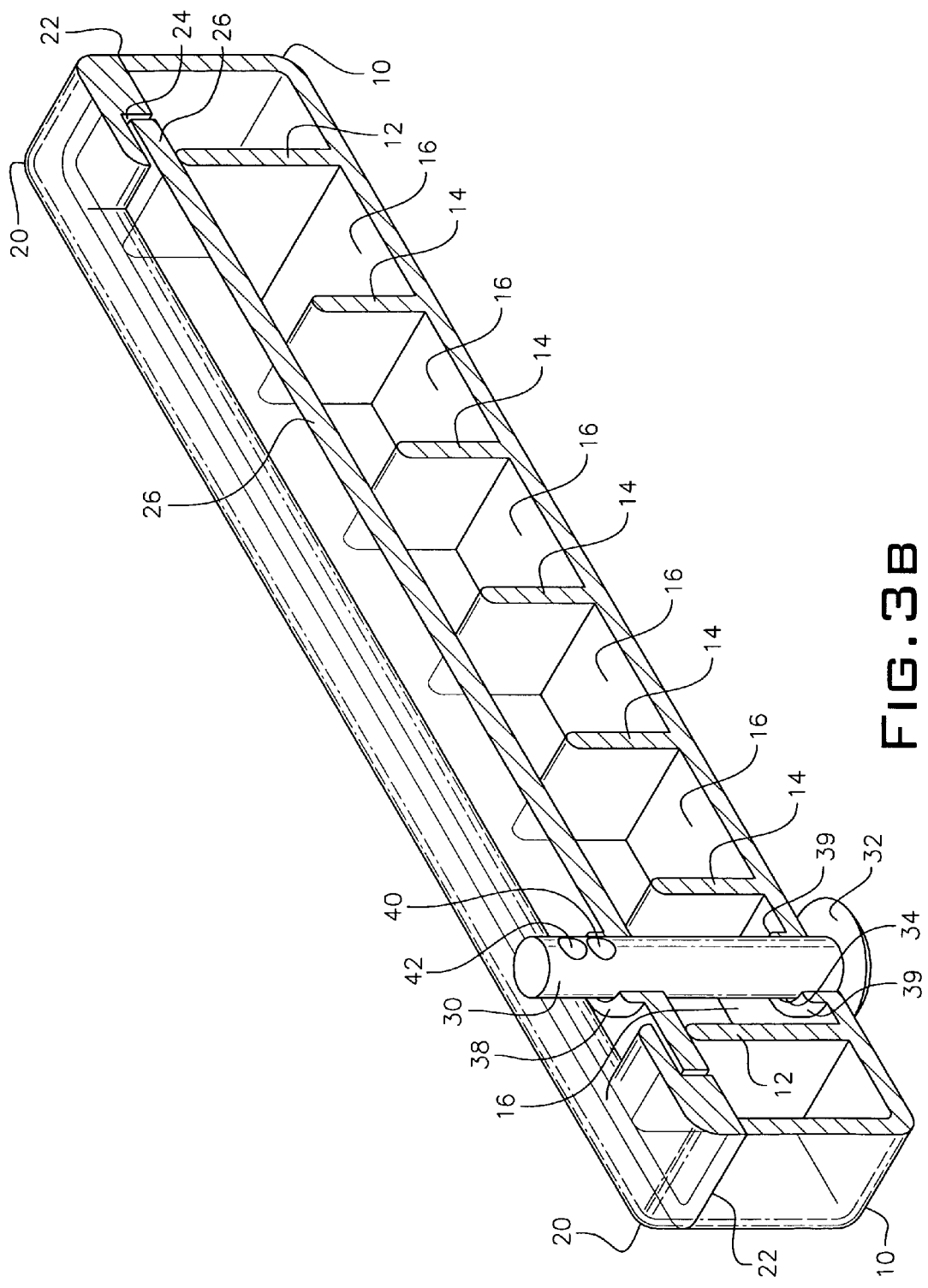

us 7,654,388 B2

APPARATUS TO SECURE AND FACILITATE THE INVENTORY OF MEDICATIONS IN EMERGENCY MEDICAL SERVICES VEHICLES

CROSS-REFERENCES TO RELATED APPLICATIONS

Not applicable.

STATEMENT REGARDING FEDERALLY SPONSORED RESEARCH OR DEVELOPMENT

Not applicable.

MICROFICHE APPENDIX

Not applicable.

BACKGROUND OF THE INVENTION

1. Field of the Invention

This invention relates to the field of strong boxes, safes, and other lockable containers, particularly those for use in ambulances and other emergency services vehicles to secure controlled substances.

2. Description of Related Art

Advanced Life Support (ALS) and air ambulance service providers are commonly required by state and federal regulatory authorities to develop, implement, maintain, and have available for review and approval by those authorities written operating procedures for procuring, storing, handling, dispensing, and disposal of all controlled substances, medications, and fluids employed in connection with those services. In particular, the security procedures submitted by a provider typically must include the provider's method of ensuring against theft; tampering with, or contamination of, controlled substances, medications, and fluids; and the identities and position titles of employees who have access to controlled substances.

Providers must be able to document the amount of each controlled substance in on-site storage, and therefore must track the distribution, disposal, and re-supply of controlled substances, medications, and fluids. Procedures for developing and maintaining such documentation must address on-site and shift change inventory procedures for all controlled substances stocked by the provider, and identify a procedure for keeping records, including inventory schedules for stocking of medical supplies and reporting and resolving any discrepancy found during an inventory.

Providers currently employ opaque narcotics storage containers manufactured of metal, plastic, or other materials. These containers may be secured from tampering by way of a numbered tamper-resistant break lock, pull-tight seal. An unbroken seal ensures that the box has not been opened, whereas any break in the seal suggests that the box may have been opened.

Because the tamper-resistant seals are easily compromised, their function is limited to providing information regarding possible tampering. In order to actually prevent unauthorized access to the controlled substances, the narcotics box is separately secured by a lock or the box itself is placed into a larger lockable storage container on or within the emergency vehicle, or both. Frequently, the storage container is rigidly secured to the vehicle, more or less permanently.

Emergency vehicles usually carry at all times standard quantities and types of controlled substances—typically, morphine, Versad, and Diazepam —in tamper-resistant glass ampules, which are stored in the narcotics container on board. Documentation procedures to track storing, handling, dispensing, and disposal of these controlled substances ordinarily will detail information about the narcotics container and the medications contained in them. This information generally includes the date and time the container was last inspected and sealed, the number of the seal, and the identity of the person who last inspected and sealed the container. Inventory information regarding the contents of the container would normally include the types, amounts, unit control numbers, and expiration dates of medications, as reflected on the labels of the ampules. Any use or disposal (e.g., due to expiration or damage) of any medications must also be documented.

When the emergency personnel on a vehicle change shifts, an individual coming on shift must confirm that the documentation generated by those coming off shift reflects properly the contents and condition of the narcotics container. Because the narcotics containers currently used by providers are opaque, the seal on a container must be broken and the container opened in order to confirm the identity of the medications in the container and their respective unit control numbers, expiration dates, and general condition. Moreover, individual ampules often must be handled physically in order to observe their respective labels and the condition of their respective tamper-resistant seals, which handling can itself lead to impairment of the integrity of the individual seals or cracking of the glass ampules and consequent loss of use of those medications. Following confirmation and documentation of the contents of the narcotics container, and replacement of any used medications, the container must be re-sealed using another numbered tamper-resistant seal. The process by which emergency medical personnel must unseal, open, and reseal narcotics containers to conduct routine, periodic drug inventories wastes time, labor, and material resources.

BRIEF SUMMARY OF THE INVENTION

The present invention comprises a totally clear, lockable, sealable container for the storage of controlled substances in ambulances and other emergency medical vehicles, allowing paramedics and other emergency medical personnel to inspect and inventory readily the pharmaceuticals in the container without opening, unlocking, or breaking the seal on the container.

BRIEF DESCRIPTION OF THE SEVERAL VIEWS OF THE DRAWINGS

FIG. 3A illustrates a cross-section of the end of the apparatus with the clevis pin removed.

FIG. 3B illustrates a cross-section of the end of the apparatus with the clevis pin inserted.

Figure 1:
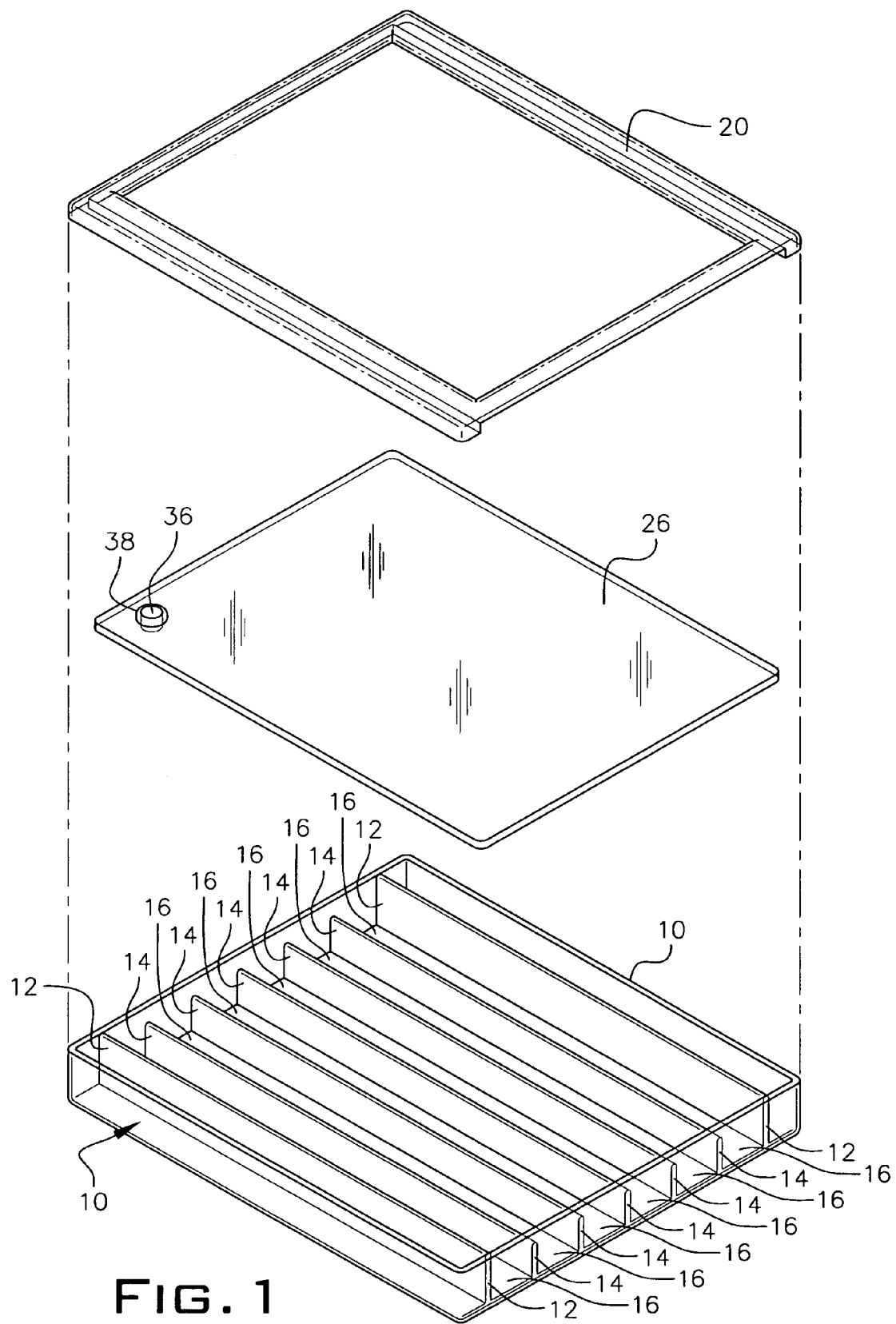
FIG. 1 presents an exploded view of the lower and upper portions of the apparatus, as well as its transparent slidable lid.

REFERENCE NUMERALS IN THE DRAWINGS 10 lower section
14 intermediate rib
18 ampule
22 seam
26 lid
30 shank
34 first hole (lower section)
38 grommet (lid)
40 third hole (shank)
44 seal
48 padlock
12 outermost rib
16 channel
20 upper section
24 slot
28 clevis pin
32 head
36 second hole (lid)
39 grommet (lower section)
42 fourth hole (shank)
46 shackle

DETAILED DESCRIPTION OF THE INVENTION

Figure 2:
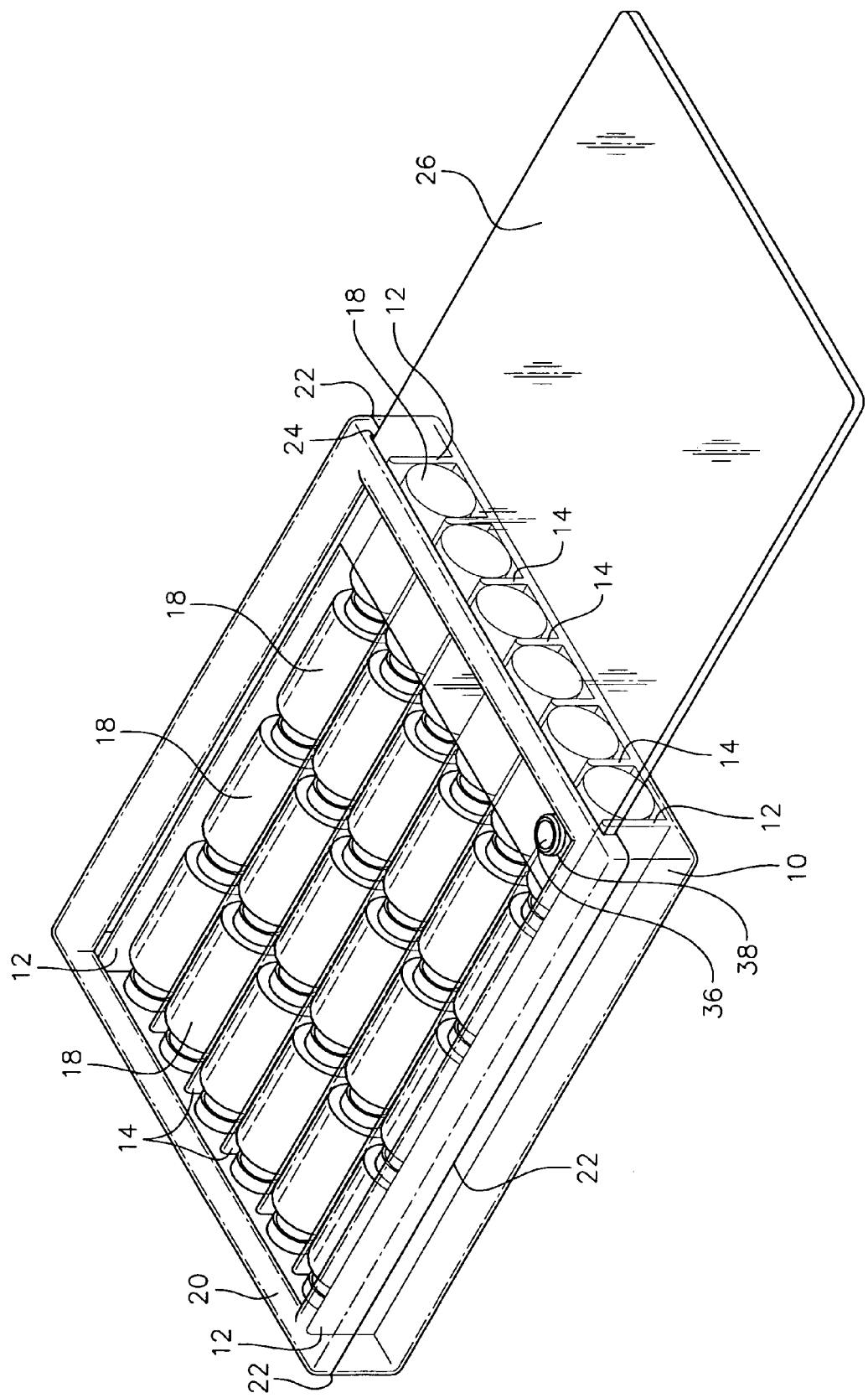
FIG. 2 illustrates the placement of ampules of medication in the slots between the ribs, the visibility of those ampules through the box, and the lower height of the intermediate ribs relative to the ampules.

An exploded view of a preferred embodiment of the container of the present invention is illustrated in FIG. 1. This embodiment, a clear box, comprises a lower section 10 having a depth forming an area to contain medications. This area is subdivided by clear, thin longitudinal ribs 12, 14 secured to and rising from the bottommost surface of the lower section, creating channels 16 between the ribs, running the length of the interior of the lower section, into which standard-sized ampules 18 of medications may be placed, as illustrated in FIG. 2.

The two outermost ribs 12 extend vertically to the uppermost edge of the lower section 10, providing structural support to a peripheral upper section 20 joining with the lower section along a seam 22. A single slot 24 at one end of the box accommodates the insertion and removal of a clear slidable lid 26. The vertical height of the intermediate ribs 14 is lower than the two outermost ribs 12 to allow for easier retrieval of ampules 18 of medication that may be placed in the channels 16 formed by the ribs 12, 14.

The overall length of both the lower section 10 and upper section 20 is approximately 7¼ inches, and the overall width of these sections is approximately 6¼ inches. When joined at the seam 22, the lower section 10 and upper section 20 together make the height of the box about 1⅛ inches. The channels 16 created by the ribs 12, 14 are approximately ¾ inches wide. The intermediate ribs 14 are about ¾ inches high. The actual dimensions of the box may be varied to achieve greater length, width, or depth. By maintaining relatively compact overall dimensions, paramedics and other emergency personnel may transport the box easily from within an ambulance or other emergency vehicle to the location of a patient requiring treatment outside the vehicle.

The box is clear from virtually all angles, enabling the contents of the box to be examined through the lid 26, through the bottom of the lower section 10, from either end, and from either side. This allows paramedics and other emergency personnel to inspect ampules 18 of drugs placed in the channels 16 between the ribs 12, 14, and to view readily their respective control numbers and expiration dates, as well as their general condition, at shift change without shaking the drugs or opening the box. To achieve the requisite transparency, as well as strength and durability, the lower section 10 and upper section 20 of the box, as well as the ribs 12, 14, may be injection molded or otherwise made from clear ABS (Acrylonitrile Butadiene Styrene) plastic or other suitable material. These sections may be joined together along a seam 22 with ABS glue, or fixed together via ultrasonic welds or tamper-resistant snaps. The lid 26 may be made of clear acrylic or similarly durable transparent material.

As seen in FIG. 3A of the drawings, which presents a cross-section view of one end of the box with the transparent slidable lid fully inserted and the clevis pin removed, there is a first hole 34 in a channel in the bottommost surface of the lower section 10 and a second hole 36 in the transparent slidable lid 26, the second hole being of roughly the same diameter as the first hole, and located immediately above the first hole 34.

FIG. 3B of the drawings, which presents a cross-section view of one end of the box with the transparent slidable lid fully inserted and the clevis pin in place, illustrates how the shank 30 of a clevis pin 28 may be passed from the exterior of the bottommost surface of the lower section through the first hole 34 in the channel in the bottommost surface of the lower section 10 and then through the second hole 36 in the transparent slidable lid 26. The head 32 of the clevis pin 28 will be flush with the exterior of the bottom surface of the lower section of the box. Grommets 38, 39 of ABS plastic or other material may be employed to reinforce these holes. The end of the shank 30 has two holes of equal size, perpendicular to the shank and parallel to one another 40, 42.

Figure 4:
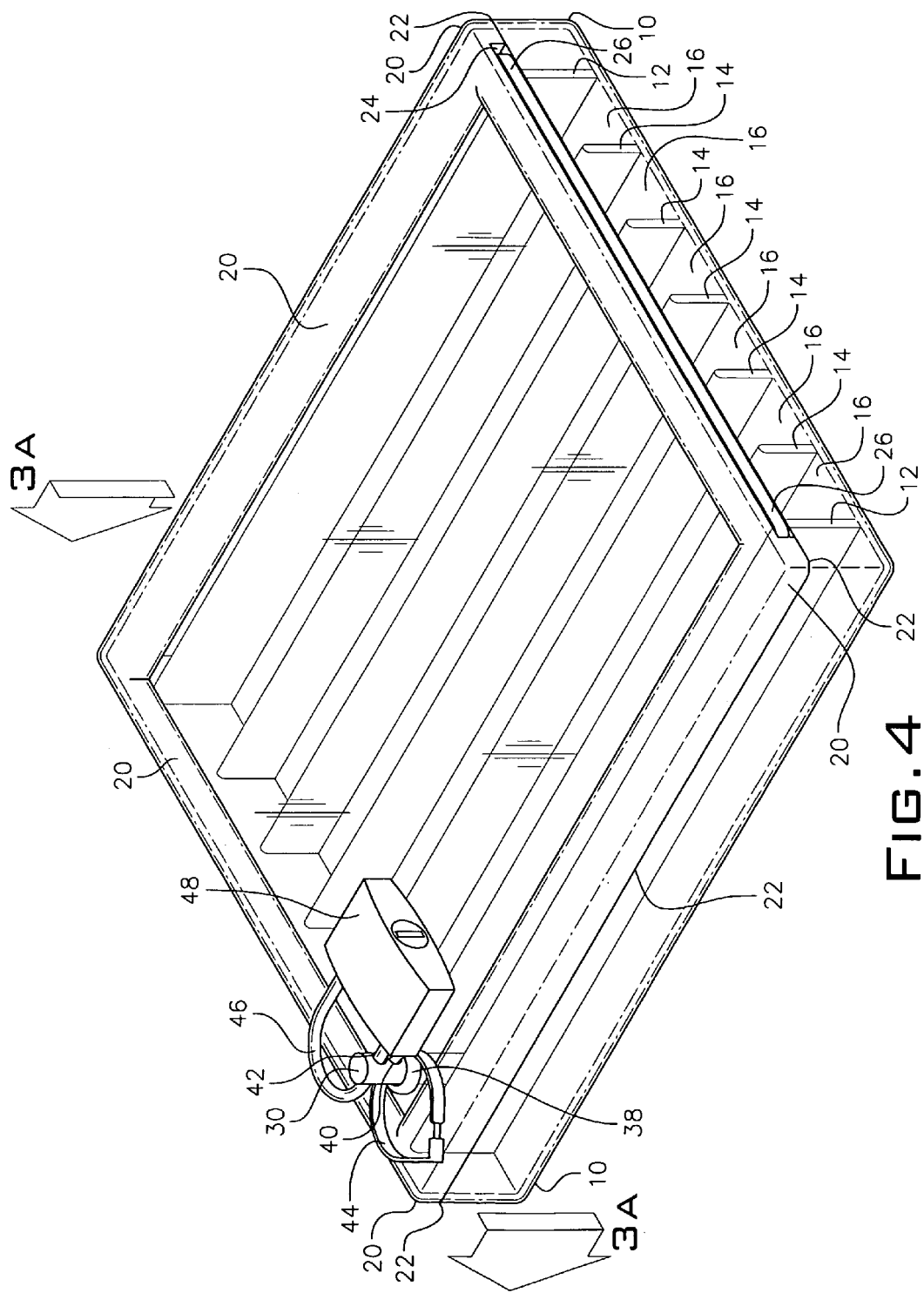
FIG. 4 is an overhead perspective view of the transparent container apparatus in a closed, sealed, and locked condition.

FIG. 4 illustrates the insertion through the holes 40, 42 in the shank 30, respectively, of a tamper-resistant, break-lock, pull-tight seal 44, and the sliding shackle 46 of a padlock 48. If the seal 44 is broken, it indicates that the box may have been opened and the contents compromised. The padlock 48, which may be individually keyed, provides security from ready access by anyone who does not have the key.

Figure 5:
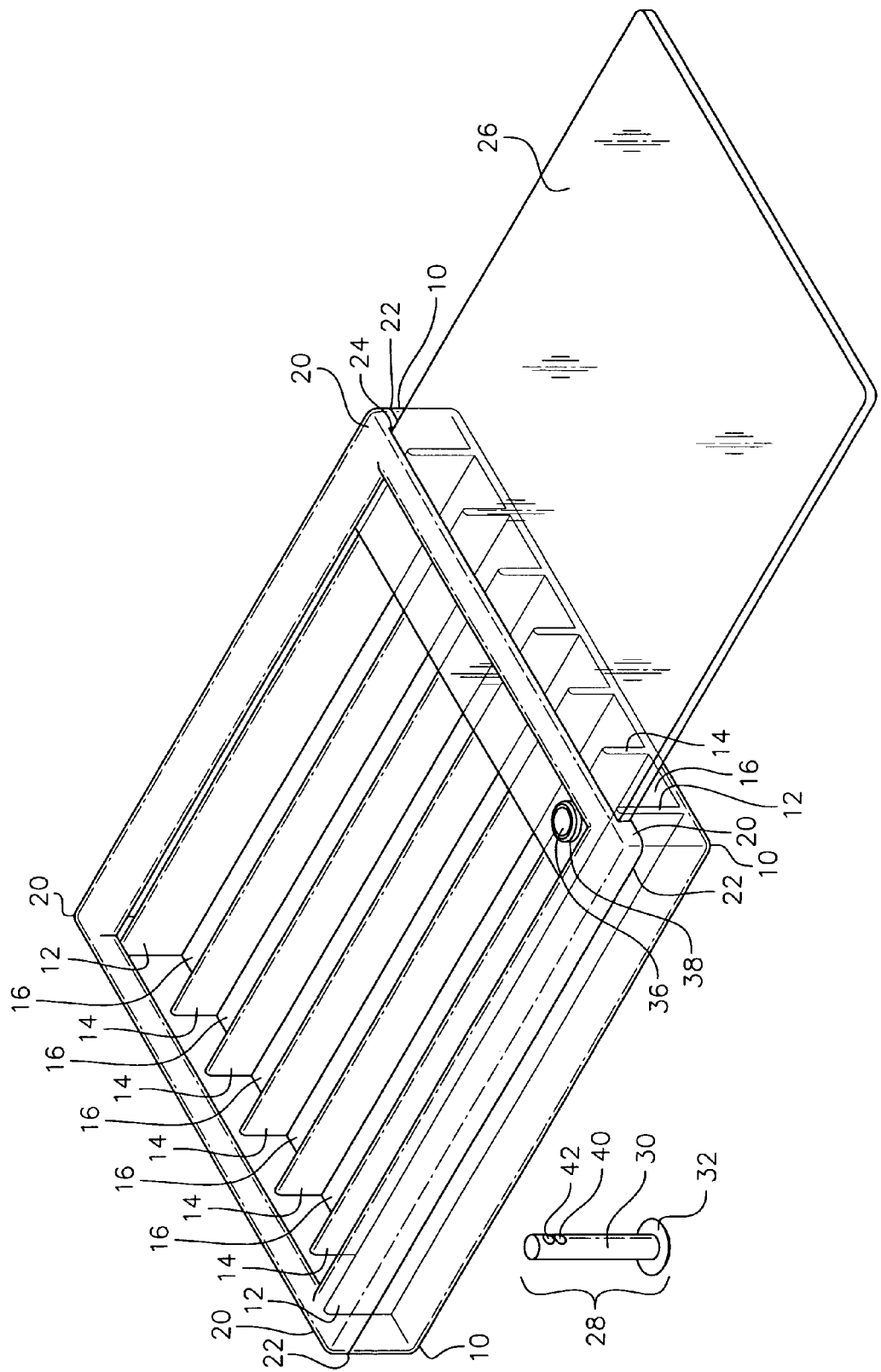
FIG. 5 is an overhead perspective of the apparatus in an open, unsealed, and unlocked condition. The removed clevis pin used to seal and lock the lid is illustrated as well.

In an open, unsealed, and unlocked condition, illustrated in FIG. 5, with the clevis pin. 28 removed, the transparent slidable lid 26 retracts through the slot 24 at one end of the box to allow access to ampules 18 of medication inside the box. A grommet 39 in the hole in the lid 26 may serve to keep the lid 26 from sliding completely out of the slot 24, thereby preventing the lid 26 from readily or inadvertently being separated from the box.

The invention claimed is:

1. A transparent lockable container for securing controlled substances on an emergency vehicle, comprising:
  a. a transparent lower section having a depth forming an interior area to contain medications, subdivided by transparent, thin longitudinal ribs secured to and rising from the bottommost surface of said lower section, said ribs creating channels running the length of said interior area of said lower section, each such channel capable of accepting one or more ampules of medication, and incorporating a first hole in one of said channels in said bottommost surface;
  b. a transparent upper section joined to the lower section along a seam;
  c. a single slot at one end of the container to accommodate the insertion and withdrawal of a transparent slidable lid;
  d. a transparent slidable lid passing through said slot, incorporating a second hole of roughly the same diameter as said first hole;
  e. a clevis pin, the shank of which is capable of being inserted from the exterior of said bottommost surface of said lower section through said first hole in said bottommost surface and then through said second hole in said lid.

2. The container of claim 1, in which said lower section and said upper section are made from Acrylonitrile Butadiene Styrene, joined together along said seam with Acrylonitrile Butadiene Styrene glue.

3. The container of claim 2, in which said lid is made of acrylic.

4. The container of claim 1, in which two outermost ribs extend vertically to an uppermost edge of said lower section, and in which intermediate ribs located between said outermost ribs extend vertically to a height lower than said outermost ribs.

5. The container of claim 4, in which said intermediate ribs are about ¾ inches high.

6. The container of claim 1, in which said channels are approximately ¾ inches wide.

7. The container of claim 1, in which the overall length of both said lower section and said upper section is approximately 7¼ inches, the overall width of said sections is approximately 6¼ inches, and the overall height of the container, when said sections are joined at said seam, is approximately 1⅛ inches.

8. The container of claim 1, in which a first grommet is inserted into said first hole.

9. The container of claim 8, in which said first grommet is made of Acrylonitrile Butadiene Styrene.

10. The container of claim 1, in which a second grommet is inserted into said second hole.

11. The container of claim 10, in which said second grommet is made of Acrylonitrile Butadiene Styrene.

12. The container of claim 1, in which third and fourth holes, each perpendicular to said shank, pass through said shank and are each capable of accommodating the insertion of either a slidable padlock shackle or a tamper-resistant, break-lock, pull-tight seal.

13. The container of claim 12 in which a padlock is used to secure the lid by passing its shackle through one of the two holes in the shank of the clevis pin, and by passing a tamper-resistant, break-lock, pull-tight seal through the remaining hole of said shank.

* * * * *